US009771332B2

(12) United States Patent
Ruggeri

(10) Patent No.: US 9,771,332 B2
(45) Date of Patent: Sep. 26, 2017

(54) 2-THIOPYRIMIDINONES

(71) Applicant: Pfizer Inc., New York, NY (US)

(72) Inventor: Roger Ruggeri, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/144,234

(22) Filed: May 2, 2016

(65) Prior Publication Data

US 2016/0326121 A1    Nov. 10, 2016

Related U.S. Application Data

(60) Provisional application No. 62/157,067, filed on May 5, 2015.

(51) Int. Cl.
| A61K 31/505 | (2006.01) |
| A61K 31/513 | (2006.01) |
| C07D 239/56 | (2006.01) |
| A61K 45/06 | (2006.01) |

(52) U.S. Cl.
CPC .......... *C07D 239/56* (2013.01); *A61K 31/513* (2013.01); *A61K 45/06* (2013.01)

(58) Field of Classification Search
CPC ... A61K 31/505; A61K 31/513; C07D 239/56
USPC .......................................... 514/274; 544/312
See application file for complete search history.

(56) References Cited

U.S. PATENT DOCUMENTS

| 4,088,751 | A | 5/1978 | Kenkare et al. |
| 4,171,429 | A | 10/1979 | Watanabe et al. |
| 4,411,699 | A | 10/1983 | Iwakura et al. |
| 5,461,060 | A | 10/1995 | Miyasaka et al. |
| 5,534,534 | A | 7/1996 | Makino et al. |
| 5,612,359 | A | 3/1997 | Murugesan |
| 5,719,190 | A | 2/1998 | MacLean et al. |
| 5,747,500 | A | 5/1998 | Son et al. |
| 6,043,265 | A | 3/2000 | Murugesan et al. |
| 6,096,753 | A | 8/2000 | Spohr et al. |
| 6,130,340 | A | 10/2000 | Jacobsen et al. |
| 6,172,066 | B1 | 1/2001 | Nagarathnam et al. |
| 6,211,370 | B1 | 4/2001 | Jacobsen et al. |
| 6,228,861 | B1 | 5/2001 | Nagarathnam et al. |
| 6,245,773 | B1 | 6/2001 | Wong et al. |
| 6,268,369 | B1 | 7/2001 | Nagarathnam et al. |
| 6,444,656 | B1 | 9/2002 | Nguyen-Ba et al. |
| 6,562,966 | B2 | 5/2003 | Deng et al. |
| 6,562,967 | B2 | 5/2003 | Deng et al. |
| 6,720,324 | B2 | 4/2004 | Marzabadi et al. |
| 6,727,257 | B1 | 4/2004 | Nagarathnam et al. |
| 7,105,559 | B2 | 9/2006 | South et al. |
| 7,485,604 | B2 | 2/2009 | Negoro et al. |
| 7,485,729 | B2 | 2/2009 | Hsieh et al. |
| 7,781,584 | B2 | 8/2010 | Feng et al. |
| 7,795,428 | B2 | 9/2010 | Feng et al. |
| 7,807,689 | B2 | 10/2010 | Zhang et al. |
| 8,088,846 | B2 | 1/2012 | Hsieh et al. |
| 8,173,663 | B2 | 5/2012 | Feng et al. |
| 8,236,446 | B2 | 8/2012 | Lu |
| 8,277,691 | B2 | 10/2012 | Lu |
| 8,288,539 | B2 | 10/2012 | Feng et al. |
| 8,835,449 | B2 | 9/2014 | Conn et al. |
| 8,841,314 | B2 | 9/2014 | Hepworth et al. |
| 9,399,626 | B2 | 7/2016 | Carpino et al. |
| 2002/0151744 | A1 | 10/2002 | Deng et al. |
| 2003/0069261 | A1 | 4/2003 | Marzabadi et al. |
| 2004/0029742 | A1 | 2/2004 | Mukkamala |
| 2004/0029743 | A1 | 2/2004 | Mukkamala |
| 2004/0220148 | A1 | 11/2004 | Stilz et al. |
| 2004/0242609 | A1 | 12/2004 | Marzabadi et al. |
| 2004/0259864 | A1 | 12/2004 | Geneste et al. |
| 2005/0014657 | A1 | 1/2005 | Negoro et al. |
| 2005/0020533 | A1 | 1/2005 | Macchia et al. |
| 2005/0222180 | A1 | 10/2005 | Fardis et al. |
| 2006/0183748 | A1 | 8/2006 | Balzarini et al. |
| 2007/0154914 | A1 | 7/2007 | Gelfand et al. |
| 2007/0213323 | A1 | 9/2007 | Imogai et al. |
| 2008/0003283 | A1 | 1/2008 | Feng et al. |
| 2008/0113993 | A1 | 5/2008 | DeBelin et al. |
| 2009/0012059 | A1 | 1/2009 | Feng et al. |
| 2009/0042863 | A1 | 2/2009 | Takeuchi et al. |
| 2009/0130689 | A1 | 5/2009 | Verdier et al. |
| 2010/0324001 | A1 | 12/2010 | Morand et al. |
| 2011/0003828 | A1 | 1/2011 | Blumberg et al. |
| 2011/0076276 | A1 | 3/2011 | Guo et al. |
| 2011/0224155 | A1 | 9/2011 | Tachdjian et al. |
| 2011/0245282 | A1 | 10/2011 | Westwood et al. |
| 2012/0292565 | A1 | 11/2012 | Delfort et al. |
| 2013/0123230 | A1* | 5/2013 | Carpino ............... A61K 31/352 514/210.2 |

FOREIGN PATENT DOCUMENTS

| AU | 2005284098 | 3/2006 |
| CA | 2252144 | 4/2000 |
| DE | 19918725 | 10/2000 |
| DE | 102009037300 | 2/2011 |
| EP | 842943 | 5/1998 |
| EP | 1586571 | 10/2005 |
| EP | 1616874 | 1/2006 |
| EP | 2181985 | 5/2010 |
| ES | 2352926 | 2/2011 |
| GB | 2090850 | 7/1982 |
| GB | 2263639 | 8/1993 |
| JP | 3261641 | 11/1991 |
| JP | 5025142 | 2/1993 |
| JP | 5025144 | 2/1993 |

(Continued)

OTHER PUBLICATIONS

Zhang, et al., "PTP1B as a drug target: recent developments in PTP1B inhibitor discovery", Drug Discovery Today, vol. 12(9/10), pp. 373-381 (2007).

(Continued)

*Primary Examiner* — Brenda Coleman
(74) *Attorney, Agent, or Firm* — A. Dean Olson

(57) ABSTRACT

Myeloperoxidase inhibitor, pharmaceutical compositions containing the inhibitor and the use of the inhibitor to treat, for example, cardiovascular conditions.

6 Claims, 1 Drawing Sheet

(56) References Cited

FOREIGN PATENT DOCUMENTS

| | | |
|---|---|---|
| JP | 5043555 | 2/1993 |
| JP | 6003761 | 1/1994 |
| JP | 7295165 | 11/1995 |
| JP | 7295166 | 11/1995 |
| JP | 2001131133 | 5/2001 |
| JP | 3781200 | 5/2006 |
| JP | 2009167179 | 7/2009 |
| JP | 2010126479 | 11/2010 |
| WO | 8910701 | 11/1989 |
| WO | 9518109 | 7/1995 |
| WO | 9614846 | 5/1996 |
| WO | 9717969 | 5/1997 |
| WO | 9741097 | 11/1997 |
| WO | 9742956 | 11/1997 |
| WO | 9824780 | 6/1998 |
| WO | 9824782 | 6/1998 |
| WO | 9851311 | 11/1998 |
| WO | 9905125 | 2/1999 |
| WO | 9936375 | 7/1999 |
| WO | 9959561 | 11/1999 |
| WO | 0001389 | 1/2000 |
| WO | 0075136 | 12/2000 |
| WO | 0140231 | 6/2001 |
| WO | 0185146 | 11/2001 |
| WO | 0193841 | 12/2001 |
| WO | 0198306 | 12/2001 |
| WO | 0206244 | 1/2002 |
| WO | 0206245 | 1/2002 |
| WO | 0206277 | 1/2002 |
| WO | 0206389 | 1/2002 |
| WO | 0210096 | 2/2002 |
| WO | 0232920 | 4/2002 |
| WO | 0233128 | 4/2002 |
| WO | 02068410 | 9/2002 |
| WO | 02069903 | 9/2002 |
| WO | 02090575 | 11/2002 |
| WO | 03011799 | 2/2003 |
| WO | 03016275 | 2/2003 |
| WO | 03028729 | 4/2003 |
| WO | 03029216 | 4/2003 |
| WO | 03029224 | 4/2003 |
| WO | 03057677 | 7/2003 |
| WO | 03072197 | 9/2003 |
| WO | 03084935 | 10/2003 |
| WO | 03084936 | 10/2003 |
| WO | 03084937 | 10/2003 |
| WO | 03084938 | 10/2003 |
| WO | 03089430 | 10/2003 |
| WO | 03093242 | 11/2003 |
| WO | 03097604 | 11/2003 |
| WO | 2004037159 | 5/2004 |
| WO | 2004073703 | 9/2004 |
| WO | 2004089927 | 10/2004 |
| WO | 2005005667 | 1/2005 |
| WO | 2005026184 | 3/2005 |
| WO | 2005063751 | 7/2005 |
| WO | 2005095381 | 10/2005 |
| WO | 2005116014 | 12/2005 |
| WO | 2006005142 | 1/2006 |
| WO | 2006022899 | 3/2006 |
| WO | 2006030032 | 3/2006 |
| WO | 2006030323 | 3/2006 |
| WO | 2006031806 | 3/2006 |
| WO | 2006046910 | 5/2006 |
| WO | 2006062465 | 6/2006 |
| WO | 2006070292 | 7/2006 |
| WO | 2006089221 | 8/2006 |
| WO | 2006131676 | 12/2006 |
| WO | 2007005774 | 1/2007 |
| WO | 2007015168 | 2/2007 |
| WO | 2007021803 | 2/2007 |
| WO | 2007023390 | 3/2007 |
| WO | 2007026252 | 3/2007 |
| WO | 2007031874 | 3/2007 |
| WO | 2007045998 | 4/2007 |
| WO | 2007064797 | 6/2007 |
| WO | 2007074884 | 7/2007 |
| WO | 2007077048 | 7/2007 |
| WO | 2007077057 | 7/2007 |
| WO | 2007120098 | 10/2007 |
| WO | 2007122482 | 11/2007 |
| WO | 2007142576 | 12/2007 |
| WO | 2007142577 | 12/2007 |
| WO | 2007143055 | 12/2007 |
| WO | 2008023249 | 2/2008 |
| WO | 2008046602 | 4/2008 |
| WO | 2008046609 | 4/2008 |
| WO | 2008065508 | 6/2008 |
| WO | 2008070447 | 6/2008 |
| WO | 2008082561 | 7/2008 |
| WO | 2008154221 | 12/2008 |
| WO | 2009005674 | 1/2009 |
| WO | 2009005693 | 1/2009 |
| WO | 2009016462 | 2/2009 |
| WO | 2009025617 | 2/2009 |
| WO | 2009025618 | 2/2009 |
| WO | 2009055917 | 5/2009 |
| WO | 2009066060 | 5/2009 |
| WO | 2009114950 | 9/2009 |
| WO | 2009120872 | 10/2009 |
| WO | 2009129120 | 10/2009 |
| WO | 2009137508 | 11/2009 |
| WO | 2009144554 | 12/2009 |
| WO | 2009144555 | 12/2009 |
| WO | 2010013161 | 2/2010 |
| WO | 2010023594 | 3/2010 |
| WO | 2010038043 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010124201 | 10/2010 |
| WO | 2010124237 | 10/2010 |
| WO | 2010128414 | 11/2010 |
| WO | 2010128425 | 11/2010 |
| WO | 2010136546 | 12/2010 |
| WO | 2010138901 | 12/2010 |
| WO | 2010140092 | 12/2010 |
| WO | 2010151689 | 12/2010 |
| WO | 2010151711 | 12/2010 |
| WO | 2011003018 | 1/2011 |
| WO | 2011005611 | 1/2011 |
| WO | 2011045415 | 4/2011 |
| WO | 2011057220 | 5/2011 |
| WO | 2011064470 | 6/2011 |
| WO | 2011094890 | 8/2011 |
| WO | 2011097300 | 8/2011 |
| WO | 2011097607 | 8/2011 |
| WO | 2011109799 | 9/2011 |
| WO | 2011163594 | 12/2011 |
| WO | 2012016133 | 2/2012 |
| WO | 2012076736 | 6/2012 |
| WO | 2013068875 | 5/2013 |

OTHER PUBLICATIONS

Jones, et al., "The Emergence of GPR119 Agonists as Anti-Diabetic Agents", Annual Reports in Medicinal Chemistry, vol. 44, pp. 149-170 (2009).

Kharitonenkov, et al., "FGF21: A novel prospect for the treatment of metabolic diseases", Current Opinion in Investigational Drugs, vol. 10(4), pp. 359-364 (2009).

Zhong, "TGR5 as a Therapeutic Target for Treating Obesity", Current Topics in Medicinal Chemistry, vol. 10, pp. 386-396 (2010).

Medina, "GPR40 (FFAR1) Modulators", Annual Reports in Medicinal Chemistry, vol. 43, pp. 75-85 (2008).

Carpino, et al., "Diabetes area participation analysis: a review of companies and targets described in 2008-2010 patent literature", Expert Opinion of Therapeutic Patents, vol. 20(12), pp. 1627-1651 (2010).

(56) References Cited

OTHER PUBLICATIONS

Gomes, et al., "Fluorescence probes used for detection of reactive oxygen species", Journal of Biochem. Biophys. Methods, vol. 65(2-3), pp. 45-80 (2005).
Neidlein, et al., "Synthesis of 3,4-and 4-Substituted Uracils and Sulfa-uracils", Archiv der Pharmazie, vol. 305(8), pp. 596-601 (1972).
Aldib, et al., "Evaluation of New Scaffolds of Myeloperoxidase Inhibitors by rational Design Combined with High-Throughput Virtual Screening", Journal of Medicinal Chemistry, vol. 55(16), pp. 7208-7218 (2012).
Tiden, et al., "2-Thioxanthines Are Mechanism-based Inactivators of Myeloperoxidase That Block Oxdative Stress during Inflammation", The Journal of Biological Chemistry, vol. 286(43), pp. 37578-37589 (2011).
Malvezzi, et al., "MPO Inhibitors Selected by Virtual Screening", Molecular Informatics, vol. 30(6-7), pp. 605-613 (2011).
Diaz-Ruiz, et al., "Delayed administration of dapsone protects from tissue damage and improves recovery after spinal cord injury", Journal of Neuroscience Research, vol. 89(3), pp. 373-380 (2011).
Soubhye, et al., "Structure-Based Design, Synthesis, and Pharmacological Evaluation of 3-(Aminoalkyl)-5-fluroindoles as Myeloperoxidase Inhibitors", Journal of Medicinal Chemistry, vol. 53(24), pp. 8747-8759 (2010).
Van Antwerpen, et al., "Conception of myeloperoxidase inhibitors derived from flufenamic acid by computational docking and structure modification", Bioorganic & Medicinal Chemistry, vol. 16(4), pp. 1702-1720 (2008).
Van Antwerpen, et al., "Inhibition of the myeloperoxidase chlorinating activity by non-steroidal anti-inflammatory drugs: Flufenamic acid and its 5-chloro-derivative directly interact with a recombinant human myeloperoxidase to inhibit the synthesis of hypochlorous acid", European Journal of Pharmacology, vol. 570(1-3), pp. 235-243 (2007).
Soyer, et al., "Synthesis of some 2(3H)-Benzoxazolone Derivatives and their in-vitro Effects on Human Leukocyte Myeloperoxidase Activity", Archiv der Pharmazie, vol. 338(9), pp. 405-410 (2005).
Choi, et al., "Ablation of the inflammatory enzyme myeloperoxidase mitigates features of Parkinson's disease in mice", The Journal of Neuroscience, vol. 25(28), pp. 6594-6600 (2005).
Bekesi, et al., "Effect of inhibitors of myeloperoxidase on the development of aortic atherosclerosis in an animal model", Experimental Gerontology, vol. 40(3), pp. 199-208 (2005).
Yea, et al., "Identification of a myeloperoxidase inhibitor", Clinical and Experimental Immunology, vol. 84(2), pp. 347-352 (1991).
Egan, et al., "Naphthalenes as inhibitors of myeloperoxidase: direct and indirect mechanisms of inhibition", Agents and Actions, vol. 29(3-4), pp. 266-276 (1990).
Humphreys, et al., "Role of myeloperoxidase in the killing of *Staphylococcus aureus* by human neutrophils: studies with the myeloperoxidase inhibitor salicylhydroxamic acid", Journal of General Microbiology, vol. 135(5), pp. 1187-1193 (1989).
Pincemail, et al., "Human myeloperoxidase activity is inhibited in vitro by quercetin. Comparison with three related compounds", Experientia, vol. 44(5); pp. 450-453 (1988).

Neidlein, et al., "Synthesis of 2-Amino-4-alkylmercapto-6-aryl-I,3,5-triazines and 4-Amino-6-alkyl-mercapto-2-aryl-5-pyrimidine carbonitrile", Archiv Der Pharmazie, vol. 305(9), pp. 689-691 (1972).
Neidlein, et al., "Synthesis and Characteristics of some 1,2,4-Thiadiazol-Sulfenyl Chlorides", Archiv Der Pharmazie, vol. 305(5), pp. 373-379 (1972).
Neidlein, et al., "Notes on the reaction behavior of sulfenyl chloride derivatives", Archiv Der Pharmazie, vol. 305(3), pp. 183-187 (1972).
Medda, et al., "N1-Benzyl substituted cambinol analogues as isozyme selective inhibitors of the sirtuin family of protein deacetylases", Med. Chem. Commun., vol. 2, pp. 611-615 (2011).
Berger, et al., "Peripheral artery disease, biomarkers and darapladib", American Heart Journal, vol. 161(5), pp. 972-987 (2011).
Bundgaard, Design of Prodrugs, p. 1, 1985.
Banker, et al., Modern Pharmaceutics, Third Edition, Revised and Expanded, Prodrugs, pp. 451 and 596 (1996).
Wolff, "Some consideration for prodrug design," Burger's Medicinal Chemistry and Drug Discovery, 5th Edition, vol. I: Principles and Practice, pp. 975-977, 1995.
Ruggeri, et al. "Discovery of 2-(6-(5-Chloro-2-methoxyphenyl)-4-oxo-2-thioxo-3,4-dihydropyrimidin-1(2H)-yl) acetamide (PF-06282999): A Highly Selective Mechanism-Based Myeloperoxidase Inhibitor for the Treatment of Cardiovascular Disease", Journal of Medicinal Chemistry, vol. 58, pp. 8513-8528 (2015).
Zheng, et al., "PF-1355, A Mechanism-Based Myeloperoxidase Inhibitor, Prevents Immune Complex Vasculitis and Anti-Glomerular Basement Membrane Glomerulonephritis", JPET, vol. 353(2), pp. 288-298 (2015).
Hruba, et al., "Simultaneious Inhibition of Fatty Acid Amide Hydrolase and Monoacylglycerol Lipase Shares Discriminitive Stimulus Effects with Delta9-Tetrahydrocannabinol in Mice" JPET, vol. 353(2), pp. 261-268 (2015).
Kashiwagi, et al. "The Novel Prostaglandin I2 Mimetic ONO-1301 Escapes Desensitization in an Antiplatelet Effect Due to its Inhibitory Action on Thromboxane A2 Synthesis in Mice", JPET, vol. 353(2), pp. 269-278 (2015).
Schiebl, et al., "In vivo Visualization of the Antialbuminuric Effects of the Angiotensin-Converting Enzyme Inhibitor Enalapril", JPET, vol. 353(2), pp. 299-306 (2015).
Dong, et al., "Pharmacokinetics and Disposition of the Thiouracil Derivative PF-06282999, an Orall Bioavailable, Irreversible Inactivator of Myeloperoxidase Enzyme, Across Animals and Humans", Drug Metabolism and Disposition, vol. 44(2), pp. 209-219 (2016).
Eng, et al., "Species Differences in the Oxidative Desulfurization of a Thiouracil-Based Irreversible Myeloperoxidase Inactivator by Flavin-Containing Monooxygenase Enzymes", Drug Metabolism and Disposition, vol. 44(8), pp. 1262-1269 (2016).
Carpino, et al., U.S. Appl. No. 15/191,943 (Applicant: Pfizer Inc.), filed Jun. 24, 2016.

\* cited by examiner

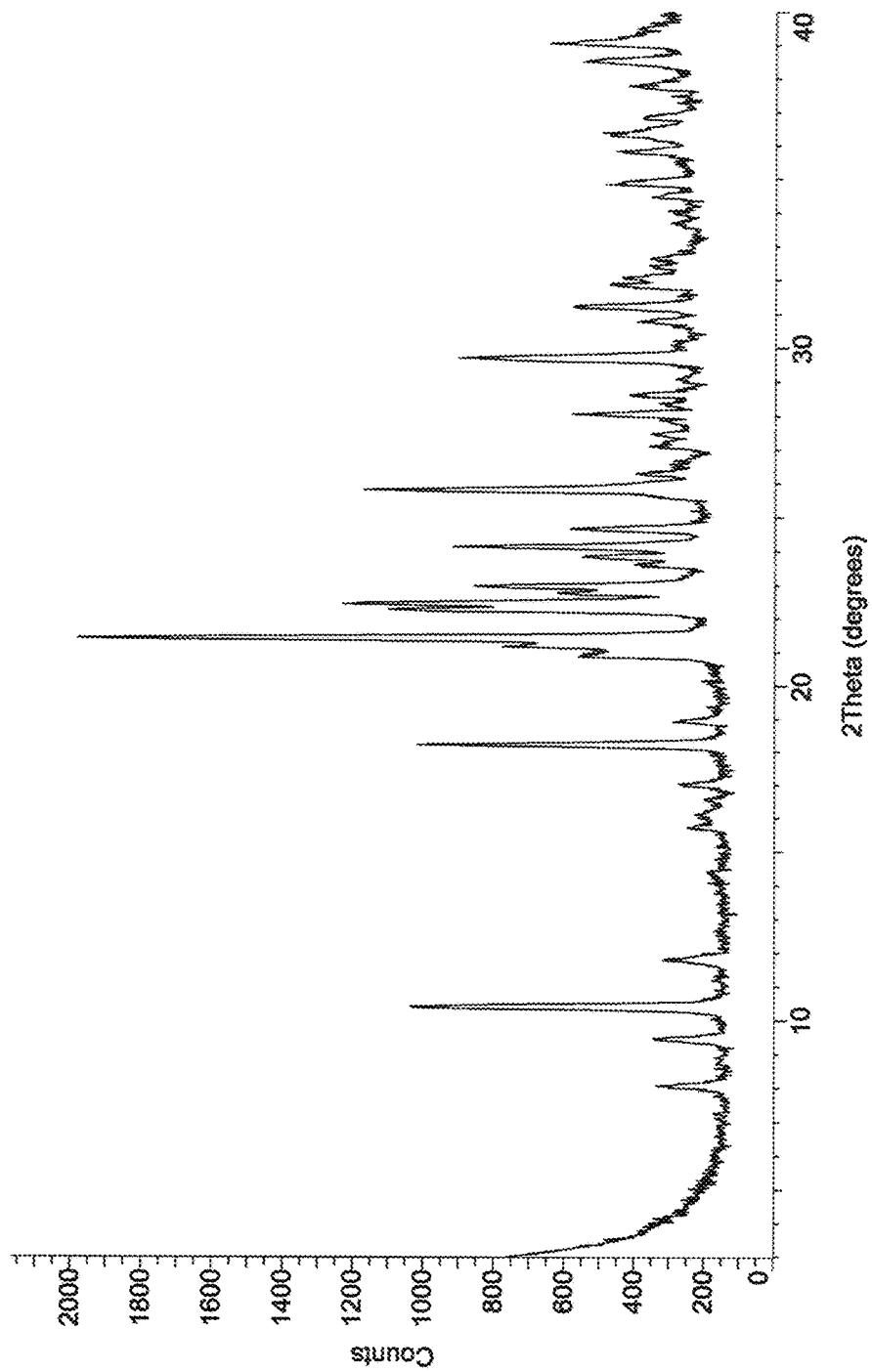

2-THIOPYRIMIDINONES

BACKGROUND OF THE INVENTION

This invention relates to myeloperoxidase inhibitors, pharmaceutical compositions containing such inhibitors and the use of such inhibitors to treat for example, cardiovascular conditions including acute coronary syndrome.

Myeloperoxidase (MPO) is a heme-containing enzyme belonging to the peroxidase superfamily. Examples of animal peroxidases are lactoperoxidase, thyroid peroxidase (TPO), eosinophil peroxidase and myeloperoxidase. Myeloperoxidase is present in primary granules of neutrophils and to a lesser extent in monocytes. It catalyzes the synthesis of hypochlorous acid from chloride and hydrogen peroxide. The hypochlorous acid formed is a powerful oxidant that reacts with a variety of cellular substrates including heme proteins, porphyrins, thiols, iron sulfur centers, nucleotides, DNA, unsaturated lipids, amines and amino acids.

In addition, MPO-catalyzed reactions and their products have been found to exhibit pro-atherogenic biological activity during the development of atherosclerosis and cardiovascular disease. For example, the myeloperoxidase plasma content is correlated with the appearance of cardiovascular disorders in patients suffering unstable angina pectoris. Myeloperoxidase has been reported to contribute to the development of atherosclerosis by the oxidation of lipids and protein in LDL and HDL.

Furthermore, it has been observed that MPO-generated oxidants reduce the bioavailability of nitric oxide, an important vasodilator. Accordingly, high MPO plasma levels are inversely correlated with the success of therapy to establish reperfusion of occluded arteries. High MPO levels are also associated with decreased survival from congestive heart failure. Additionally, it has been shown that MPO plays a role in plaque destabilization which leads to plaque rupture and myocardial infarction.

Therefore, MPO is thought to play a role in several processes that lead to cardiovascular disease including 1) impaired cholesterol trafficking and progression of the atherosclerotic plaque towards an unstable state, 2) destabilization of the atherosclerotic plaque and plaque rupture, 3) consumption of nitric oxide leading to impaired endothelial function and blood flow, and 4) pathological tissue damage post ischemia contributing to atrial fibrillation and adverse cardiac remodeling with left ventricular hypertrophy leading to congestive heart failure, aortic aneurysm, and cerebral aneurysm. As such inhibitors of MPO activity are proposed to offer significant therapeutic benefit in the prevention and treatment of cardiovascular disease.

Commonly assigned related WO 2013/068875 published on May 16, 2013 discloses a series of 2-thiopyrimidinones useful as MPO inhibitors including the inhibitor compound of Example 427.

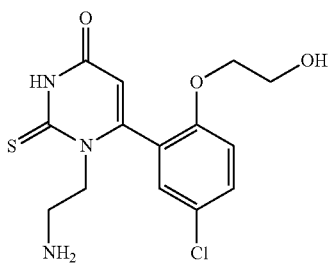

Example 427

Also related are commonly assigned U.S. Pat. No. 8,835,449 granted on Sep. 16, 2014 and first published as US 2013123230 on May 16, 2013 which discloses 2-(6-(5-chloro-2-methoxyphenyl)-4-oxo-2-thioxo-3,4-dihydropyrimidin-1(2H)-yl)acetamide (Example 1) and commonly assigned U.S. Pat. No. 8,884,314 granted on May 2, 2013 and first published as US201313296351 on Nov. 7, 2013 which discloses N-(2-aminoethyl)-2-[6-(2,4-dimethoxyphenyl)-4-oxo-2-thioxo-3,4-dihydropyrimidin-1(2H)-yl]acetamide (Example 241).

Nevertheless, although MPO has been implicated extensively in the etiology and progression of cardiovascular disease there is still an ongoing need for improved MPO inhibitors. Accordingly, there remains a need for pharmaceutical agents that have myeloperoxidase inhibiting activity and are useful in the treatment, prevention or diminution of the manifestations of the maladies described herein.

SUMMARY OF THE INVENTION

The present invention is directed to a compound of the Formula I

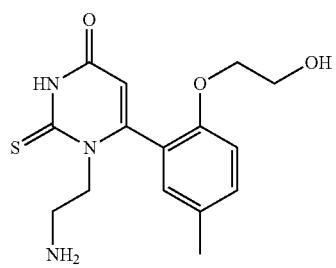

Formula I or a pharmaceutically acceptable salt thereof.

An especially preferred aspect of this invention is the hydrochloride salt of the compound of Formula I.

Another preferred aspect of this invention is the compound 1-(2-aminoethyl)-6-(2-(2-hydroxyethoxy)-5-methylphenyl)-2-thioxo-2,3-dihydropyrimidin-4(1H)-one (Compound A).

This invention is also directed to a method for treating cardiovascular events and conditions comprising administering to a mammal in need of such treatment a therapeutically effective amount of Formula I compound or a pharmaceutically acceptable salt of said compound wherein the cardiovascular condition or event is heart failure, congestive heart failure, peripheral arterial disease, pulmonary hypertension, vasculitis, a primary or secondary myocardial infarction, ischemia, ischemia reperfusion injury, atrial fibrillation, unstable angina, coronary artery disease, stroke or coronary artery bypass graft surgery (CABG).

This invention is also directed to a method for treating a condition comprising administering to a mammal in need of such treatment a therapeutically effective amount of a Formula I compound or a pharmaceutically acceptable salt of said compound wherein the condition is diabetes, renal insufficiency, dialysis, delayed graft function, transplant organ rejection or nephropathy caused by contrasting agents.

Also provided herein are compositions comprising a pharmaceutically effective amount of the Formula I compound described herein and a pharmaceutically acceptable carrier, vehicle, or diluent.

This invention is also directed to pharmaceutical combination compositions comprising: a therapeutically effective amount of a composition comprising a first compound, said first compound being a Formula I compound or a pharmaceutically acceptable salt of said compound;

a second compound, said second compound being an angiotensin converting enzyme inhibitor, an HMG-CoA reductase inhibitor, a neprilysin inhibitor, a non-steroidal anti-inflammatory agent, a Factor Xa inhibitor or warfarin; and/or optionally a pharmaceutical carrier, vehicle, or diluent.

All patents and patent applications referred to herein are hereby incorporated by reference.

Other features and advantages of this invention will be apparent from this specification and the appendant claims which describe the invention.

BRIEF DESCRIPTION OF THE DRAWINGS

The FIGURE is a characteristic x-ray powder diffraction pattern showing a crystalline form of Example 1; Preparation 5 (Vertical Axis: Intensity (CPS); Horizontal Axis: Two theta (degrees)).

DETAILED DESCRIPTION OF THE INVENTION

Preferred cardiovascular conditions include heart failure, congestive heart failure, atrial fibrillation, peripheral arterial disease, pulmonary hypertension, coronary artery disease, or vasculitis.

Other preferred cardiovascular conditions include unstable angina or a patient that has experienced a myocardial infarction as well as ischemic or hemorrhagic stroke.

The term Formula I compound as used herein refers to the Formula I compound and also includes the salts, polymorphs, isomers, tautomers, zwitterions, complexes, isotopes and the like as described below.

Pharmaceutically acceptable salts of the Formula I compound include the acid addition and base salts thereof. Acid salts of the Formula I compound are preferred. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. While base salts are not preferred, exemplary base salts include the aluminum, arginine, calcium, choline, diethylamine, glycine, lysine, magnesium, meglumine, olamine, potassium, sodium, trimethylamine and zinc salts. Hem isalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002).

The Formula I compound may exist in both unsolvated and solvated forms. The term 'solvate' is used herein to describe a molecular complex comprising the compound of the invention and one or more pharmaceutically acceptable solvent molecules, for example, ethanol and/or water. Such solvent molecules are those commonly used in the pharmaceutical art, which are known to be innocuous to the recipient, e.g., water, ethanol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The term 'hydrate' is employed when said solvent is water. Pharmaceutically acceptable solvates include hydrates (e.g., polyhydrates; monohydrates) and other solvates wherein the solvent of crystallization may be isotopically substituted, e.g. $D_2O$, $d_6$-acetone, $d_6$-DMSO. The solvates and/or hydrates preferably exist in crystalline form.

Included within the scope of the Formula I compound are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Where the compound contains, for example, a keto or thiocarbonyl group or an aromatic moiety, tautomeric isomerism ('tautomerism') can occur. It follows that a single compound may exhibit more than one type of isomerism. For example, the following is illustrative of tautomers of the compounds of Formula I.

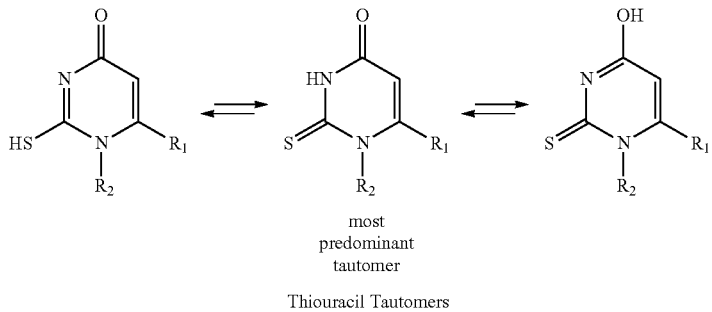

most predominant tautomer

Thiouracil Tautomers

Included within the scope of the Formula I compound are all tautomeric forms of the Formula I compound including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled Formula I compounds wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled Formula I compound, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

An isotopically-labelled Formula I compound can generally be prepared by conventional techniques known to those skilled in the art or by processes analogous to those described in the accompanying Examples and Preparations using an appropriate isotopically-labelled reagent in place of the non-labelled reagent previously employed. References herein to "treat", "treating", "treatment" and the like include curative, palliative and prophylactic treatment.

As used herein, the expressions "reaction-inert solvent" and "inert solvent" refer to a solvent or a mixture thereof which does not interact with starting materials, reagents, intermediates or products in a manner which adversely affects the yield of the desired product.

By "pharmaceutically acceptable" is meant the carrier, vehicle, or diluent and/or salt must be compatible with the other ingredients of the formulation, and not deleterious to the recipient thereof.

The term "pharmaceutically effective amount", as used herein, refers to an amount of the Formula I compound (or a combination agent or a Formula I compound in combination with a combination agent) sufficient to treat, prevent onset of or delay or diminish the symptoms and physiological manifestations of the indications described herein.

The term "room temperature or ambient temperature" means a temperature between 18 to 25° C., "HPLC" refers to high pressure liquid chromatography, "MPLC" refers to medium pressure liquid chromatography, "TLC" refers to thin layer chromatography, "MS" refers to mass spectrum or mass spectroscopy or mass spectrometry, "NMR" refers to nuclear magnetic resonance spectroscopy, "DCM" refers to dichloromethane, "DMSO" refers to dimethyl sulfoxide, "DME" refers to dimethoxyethane, "EtOAc" refers to ethyl acetate, "MeOH" refers to methanol, "Ph" refers to the phenyl group, "Pr" refers to propyl, "trityl" refers to the triphenylmethyl group, "ACN" refers to acetonitrile, "DEAD" refers to diethylazodicarboxylate, and "DIAD" refers to diisopropylazodicarboxylate.

The starting materials and reagents for the above described Formula I compound are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Cis/trans isomers may be separated by conventional techniques well known to those skilled in the art, for example, chromatography and fractional crystallization.

Pharmaceutically acceptable salts of the Formula I compound may be prepared by one or more of three exemplary methods:
(i) by reacting the Formula I compound with the desired acid or base;
(ii) by removing an acid- or base-labile protecting group from a suitable precursor of the Formula I compound, for example treating an O-tert-butylcarbamate with acid, -or by ring-opening a suitable cyclic precursor, for example, a lactone or lactam, using the desired acid or base; or
(iii) by converting one salt of the Formula I compound to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Certain processes for the manufacture of the compound of this invention are provided as further features of the invention and are described in the experimental section.

The Formula I compound of this invention may also be used in conjunction with other pharmaceutical agents (e.g., antiatherosclerotic and antithrombotic agents) for the treatment of the disease/conditions described herein.

Combination Agents

The Formula I compound can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition e.g., cardiovascular condition such as acute coronary syndrome.

Additional therapeutic agents include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor agonist), anti-thyroid agents (e.g.; propylthiouracil, methimazole, and carbimazole), anti-infective agents, anti-viral agents, anti-bacterial agents, and anti-fungal agents.

Agents used in an ICU setting are included, for example, dobutamine, dopamine, epinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent.

Exemplary factor Xa inhibitors include apixaban and rivaroxaban.

Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicylic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents include: Class I agents (such as propafenone); Class II agents (such as metoprolol, atenolol, carvedilol and propranolol); Class III agents (such as sotalol, dofetilide, amiodarone, azimilide and ibutilide); Class IV agents (such as diltiazem and verapamil); K+ channel openers such as $I_{Ach}$ inhibitors, and $I_{Kur}$ inhibitors (e.g., compounds such as those disclosed in WO01/40231).

The Formula I compound may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamterene, am iloride, spironolactone); renin inhibitors; ACE inhibitors (e.g., captopril, zofenopril, fosinopril, enalapril, ceranopril, cilazopril, delapril, pentopril, quinapril, ram ipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mibefradil.

Examples of suitable cardiac glycosides include digitalis and ouabain.

In one embodiment, a Formula I compound may be co-administered with one or more diuretics. Examples of suitable diuretics include (a) loop diuretics such as furosemide (such as LASIX™), torsemide (such as DEMADEX™), bumetanide (such as BUMEX™), and ethacrynic acid (such as EDECRIN™); (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a Formula I compound may be co-administered with a loop diuretic. In still another embodiment, the loop diuretic is selected from furosemide and torsemide. In still another embodiment, a Formula I compound may be co-administered with furosemide. In still another embodiment, a Formula I compound may be co-administered with torsemide which may optionally be a controlled or modified release form of torsemide.

In another embodiment, a Formula I compound may be co-administered with a thiazide-type diuretic. In still another embodiment, the thiazide-type diuretic is selected from the group consisting of chlorothiazide and hydrochlorothiazide. In still another embodiment, a Formula I compound may be co-administered with chlorothiazide. In still another embodiment, a Formula I compound may be co-administered with hydrochlorothiazide.

In another embodiment, a Formula I compound may be co-administered with a phthalimidine-type diuretic. In still another embodiment, the phthalimidine-type diuretic is chlorthalidone.

Examples of suitable combination mineralocorticoid receptor antagonists include sprionolactone and eplerenone.

Examples of suitable combination phosphodiesterase inhibitors include: PDE III inhibitors (such as cilostazol); and PDE V inhibitors (such as sildenafil).

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipoxygenase inhibitors; cholesterol absorption inhibitors; and cholesteryl ester transfer protein inhibitors.

Anti-inflammatory agents also include sPLA2 and IpPLA2 inhibitors (such as darapladib), 5 LO inhibitors (such as atrelueton), p38 inhibitors (such as losmapimod), and IL-1 and IL-1 r antagonists (such as canakinumab), Other atherosclerotic agents include agents that modulate the action of PCSK9.

Cardiovascular complications of type 2 diabetes are associated with deleterious levels of MPO; accordingly, the compounds of the present invention may be used in combination with anti-diabetic agents, particularly type 2 anti-diabetic agents. Examples of suitable anti-diabetic agents include (e.g. insulins, metformin, DPP-IV inhibitors, GLP-1 agonists, analogues and mimetics, SGLT1 and SGLT2 inhibitors) Suitable anti-diabetic agents include an acetyl-CoA carboxylase- (ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

Those skilled in the art will recognize that the compounds of this invention may also be used in conjunction with other cardiovascular or cerebrovascular treatments including PCI, CABG, heart transplant, kidney transplant, stenting, drug eluting stents, stem cell therapy and medical devices such as implanted pacemakers, defibrillators, or cardiac resynchronization therapy.

Myeloperoxidase activity has been demonstrated in neuroinflammatory conditions, accordingly, the compounds of the present invention may be used in combination with neuroinflammatory and neurodegenerative agents in mammals. Examples of additional neuroinflammatory and neurodegenerative agents include antidepressants, antipsychotics, anti-pain agents, anti-Alzheimer's agents, and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotrophin releasing factor (CRF) antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, nortriptyline, protriptyline, amoxapine, desipramine and maprotiline. Examples of suitable SSRIs include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable SNRIs of use in the present invention include venlafaxine. Examples of suitable atypical anti-depressants include bupropion, lithium, trazodone and viloxazine. Examples of anti-Alzheimer's agents include NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A receptor (5-HT1A) agonists, and CRF antagonists. Suitable benzodiazepines include alprazolam, chlordiazepoxide, clonazepam, chlorazepate, diazepam, lorazepam, oxazepam, and prazepam. Suitable 5-HT1A receptor agonists include buspirone and ipsapirone. Suitable CRF antagonists include verucerfont. Suitable atypical antipsychotics include paliperidone, ziprasidone, risperidone, aripiprazole, olanzapine, and quetiapine. Suitable nicotine acetylcholine agonists include CP-601927 and varenicline. Anti-pain agents include pregabalin, gabapentin, clonidine, neostigmine, baclofen, midazolam, ketamine and ziconotide.

Those skilled in the art will recognize that the compounds of this invention may also be used in conjunction with immunomodulating therapies such as cyclosporine A (Sand-immune or Neoral), tacrollmus, leflunomide, deoxyspergualin, mycophenolate (e.g., Cellcept), Atgam, anti-inflammatory steroids (e.g., prednisone or dexamethasone), azathioprine, 6-mercaptopurine, rapamycin, JAK inhibitors (e.g., Xeljanz), TNF-alpha antibodies (e.g., infliximab (remicade), adalimumab (Humira), certolizumab pegol (Cimzia), golimumab (Simponi), etanercept (Enbrel)) and methotrexate.

Particularly when provided as a single dosage unit, the potential exists for a chemical interaction between the combined active ingredients. For this reason, when a Formula I compound and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In combination therapy treatment, both the Formula I compound and the other drug therapies are administered to mammals (e.g., humans, male or female) by conventional methods.

The Formula I compound and the salts thereof are all adapted to therapeutic use as agents that inhibit myeloperoxidase in mammals, particularly humans, and thus are useful for the treatment of the various conditions (e.g., those described herein) in which such action is implicated.

It is believed that myeloperoxidase is involved in the pathologic oxidation of proteins, lipids and nucleic acids and contributes to dysfunctional cholesterol metabolism, tissue damage, and organ dysfunction and can induce or contribute to the development of cardiovascular diseases and associated adverse outcomes.

The disease/conditions that can be treated in accordance with the present invention include, but are not limited to, cardiovascular conditions, diabetes (e.g., type II) and diabetic complications, vascular conditions, neuroinflammatory conditions, neurodegenerative conditions, pain, cancer, sepsis, NASH (non-alcoholic steatatohepatitis), pulmonary injury and hypertension, renal diseases, and vasculitis syndromes especially those related to ANCA (anti-neutrophil cytoplasmic antibodies) and the like.

Given the positive correlation between activation of the myeloperoxidase with the development of cardiovascular and associated disease/conditions, the Formula I compound, by virtue of the pharmacologic action, is useful for the prevention, arrestment and/or regression of atherosclerosis and its associated disease states.

It is believed that MPO exhibits pro-atherogenic biological activity during the evolution of cardiovascular disease. Furthermore, it has been observed that MPO-generated oxidants reduce the bioavailability of nitric oxide, an important vasodilator. Additionally, it has been shown that MPO plays a role in plaque destabilization by causing the activation of metalloproteinases, leading to a weakening of the fibrous cap of the plaques and subsequent plaque destabilization and rupture. Given these wide-ranging effects of MPO, MPO has thus been implicated in a wide variety of cardiovascular diseases.

Cardiovascular conditions include, but are not limited to coronary heart disease, acute coronary syndrome, ischaemic heart disease, first or recurrent myocardial infarction, secondary myocardial infarction, non-ST segment elevation myocardial infarction, or ST segment elevation myocardial infarction, ischemic sudden death, transient ischemic attack, peripheral occlusive arterial disease, angina, atherosclerosis, hypertension, heart failure (such as congestive heart failure), diastolic dysfunction (such as left ventricular diastolic dysfunction, diastolic heart failure, and impaired diastolic filling), systolic dysfunction (such as systolic heart failure with reduced ejection fraction), atrial fibrillation, arrhythmia (ventricular), ischemia, hypertrophic cardiomyopathy, sudden cardiac death, myocardial and vascular fibrosis, impaired arterial compliance, myocardial necrotic lesions, vascular damage, left ventricular hypertrophy, decreased ejection fraction, cardiac lesions, vascular wall hypertrophy, endothelial thickening, fibrinoid necrosis of coronary arteries, adverse remodeling, stroke, and the like. Also, included are venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

Cardiovascular complications of type 2 diabetes are associated with deleterious levels of MPO, accordingly, the Formula I compound may be used to treat diabetes and diabetic complications such as macrovascular disease, hyperglycemia, metabolic syndrome, impaired glucose tolerance, hyperuricemia, glucosuria, cataracts, diabetic neuropathy, diabetic nephropathy, diabetic retinopathy, obesity, dyslipidemia, hypertension, hyperinsulinemia, and insulin resistance syndrome.

In addition, linkage of myeloperoxidase activity to disease has been demonstrated in neuroinflammatory and neurodegenerative conditions. Therefore, the Formula I compound is particularly indicated for use in the treatment of neuroinflammatory and neurodegenerative conditions (i.e., disorders or diseases) in mammals including humans such as multiple sclerosis, migraine; epilepsy; Alzheimer's disease; Parkinson's disease; Multiple-System Atrophy; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism) in a mammal, preferably a human, by administering to the mammal a therapeutically effective amount of a Formula I compound.

Other inflammatory diseases or disorders include asthma, chronic obstructive pulmonary disease, cystic fibrosis, idiopathic pulmonary fibrosis, acute respiratory distress syndrome, sinusitis, rhinitis, psoriasis, dermatitis, uveitis, gingivitis, atherosclerosis, inflammatory bowel disease, renal glomerular damage, liver fibrosis, sepsis, proctitis, rheumatoid arthritis, and inflammation associated with reperfusion injury, spinal cord injury and tissue damage/scarring/adhesion/rejection.

The term "nephropathy caused by contrasting agents" includes contrasting induced nephropathy following procedures that utilize imaging agents including cardiac surgery, non-cardiac surgery and transplant surgery. Nephropathy caused by contrasting agents also includes nephropathy caused by the use of enhanced imaging contrasting agents in patients including those at risk of a primary MI or secondary MI.

The utility of the Formula I compound as a medical agent in the treatment of the above described disease/conditions in mammals (e.g. humans, male or female) is demonstrated by the activity of the compounds of this invention in conventional in vitro and in vivo assays described below. The in vivo assays (with appropriate modifications within the skill in the art) may be used to determine the activity of other agents as well as the compounds of this invention. Such assays also provide a means whereby the activities of the Formula I compound (or the other agents described herein) can be compared to each other and with the activities of other known compounds. The results of these comparisons are useful for determining dosage levels in mammals, including humans, for the treatment of such diseases.

The following protocols may of course be varied by those skilled in the art.

Human Whole Blood Assay for Irreversible Inhibition of MPO

To measure the inhibition of MPO activity in a biological system in the present invention, bioassays were performed with human whole blood that was collected from medication-free, human volunteers in heparin treated tubes (APP Pharmaceuticals, LLC, cat # NDC#63323-047-10, #4710). Blood was aliquoted and treated with different concentrations of the MPO inhibitor or vehicle control and co-treated with or without bacterial lipopolysaccharide (LPS, InVivogen) to stimulate blood leukocytes to simultaneously generate $H_2O_2$ (a required MPO substrate) and the release of MPO. After a 4 hour incubation at room temperature the plasma fraction was collected following a 2000×g centrifugation at 4° C.

The plasma fraction was divided in two for analysis of total MPO and active MPO. The total MPO content was determined using a standard sandwich ELISA (capture and detection antibodies: Cell Sciences, Cat# HP9048, and Cell Sciences, Cat# HM2164, clone 266-6K1) and calculated relative to a standard curve of purified MPO (myeloperoxidase, Calbiochem, cat#475911) that was prepared by dilution in the autologous donor plasma. The MPO activity is determined by capturing the total MPO from plasma using the capture step as described for the above ELISA method. After washing unbound plasma material including unreacted MPO inhibitor, MPO reaction substrates were added [$H_2O_2$ (2 uM) and Amplex Red (Invitrogen, Cat# A12222)] and the Vmax of the MPO-catalyzed conversion of the Amplex Red substrate to resorufin was determined by measuring the increase in fluorescence (excitation 530 nM, emission 580 nm) using a fluorescent plate reader in a kinetic analysis. The MPO activity of the captured material was compared to that obtained with a standard curve of purified MPO (myeloperoxidase, Calbiochem, cat#475911) that was prepared in autologous donor plasma. The percent of 'active' myeloperoxidase for each sample was calculated from the ratio of the active myeloperoxidase in the Amplex Red assay and the total myeloperoxidase from the ELISA for each sample. A dose response curve of the compound concentration versus MPO activity was then plotted to determine the IC50 value.

hERG Assay

All testing was carried out in CHO cells transfected with the hERG gene purchased from Millipore (PrecisiON hERG-CHO Recombinant Cell Line CYL3038). The cell line was grown in DMEM/F-12, GlutaMAX™ with 10% fetal bovine serum, 1% Penicillin-Streptomycin, 1% Geneticin and 1% of 1M HEPES buffer solution, and maintained at approximately 37° C. in a humidified atmosphere containing 5% carbon dioxide. The cells were passaged every 3-5 days based on confluency. On the day of the experiment, 50%-80% confluent cells were harvested from a 175 $cm^2$ culture flask using Detachin™. After 10 minutes of exposure to Detachin™ at 37° C., the cells were centrifuged for 1 minute at 1000 RPM. The supernatant was removed and the cell pellet was reconstituted in 5-8 mL of serum free media with 2.5% of 1M HEPES, placed on the Qstirrer™, and allowed to recover. After a ~30 minute recovery period, experiments were initiated.

hERG current was elicited and recorded using the automated Qpatch HT™ system (as described in Kutchinsky J, Friis S, Asmild M, et al. Characterization of potassium channel modulators with QPatch automated patch-clamp technology: system characteristics and performance. Assay Drug Dev Technol 2003; 1(5):685-93). The suspended cells in the Qstirrer™ were transferred to 48 individual recording chambers on a Qplate 48™ containing extracellular recording saline composed of (in mM): 138 NaCl, 5.3 KCl, 1.3 $CaCl_2$, 0.5 $MgCl_2$, 5.6 Glucose, 5 HEPES, 0.4 $MgSO_4$, 0.44 $KH_2PO_4$, 4.2 $NaHCO_3$, 0.34 $Na_2HPO_4$, and adjusted to pH 7.4±0.1 with NaOH. The intracellular recording saline was composed of (in mM): 130 KCl, 1 $MgCl_2$, 10 HEPES, 5 Mg-ATP, and 5 EGTA, and adjusted to pH 7.2±0.1 with KOH. Membrane currents were recorded at room temperature.

hERG current was elicited from a holding potential of −80 mV with a voltage step to +30 mV for 1 second, followed by a ramp back to −80 mV at 0.55 mV/ms. Test pulses were delivered at a frequency of 0.25 Hz. Up to 4 different concentrations were studied on each cell, each exposure lasting 5 minutes or until steady-state effects were observed. In a separate set of experiments, a full concentration-response relationship and an IC50 was determined for a positive control, cisapride, (Jules C. Hancox, Mark J. McPate, Aziza El Harchi, Yi hong Zhang, The hERG potassium channel and hERG screening for drug-induced torsades de pointes, Pharmacology & Therapeutics, Volume 119, Issue 2, August 2008, Pages 118-132).

Using Sophion Qpatch Assay Software, the amplitude of the peak outward hERG current upon repolarizing ramp was measured. Current amplitude was determined by taking the average of the last 5 current peaks under each treatment condition. Percent inhibition was determined by taking the ratio of the current measured at steady state in the presence of test article ($I_{Test\ article}$) versus the control current ($I_{control}$), and expressed as: % inhibition=100−($I_{Test\ article}$/$I_{Control}$)*100. When possible, a concentration-response curve was plotted and the data were fitted using Qpatch software to determine an IC50.

Table 1 below provides the myeloperoxidase inhibitory activity in human whole blood for the compound of this invention (as the HCL salt) and for certain Examples disclosed in commonly assigned WO 2013/068875 published on May 16, 2013 in accordance with the above-described assay. In addition, it provides the hERG activity and the resultant calculated therapeutic ratio of hERG IC50/MPO IC50 for these compounds.

It has surprisingly been found that the Example 1 compound of this patent application has an advantage in the hERG IC50/MPO IC50 ratio associated with cardiovascular safety in comparison to compounds C, D and E (disclosed in WO 2013/068875), as more fully described below.

In Table 1 below the MPO IC50 (as determined according to the Human Whole Blood Assay for Irreversible Inhibition of MPO provided above) reflects the compound concentration required to irreversibly inhibit 50% of the active MPO present in a sample of human blood tested exogenously. Compound A (Example 1 in this patent application), effectively inhibits MPO in human plasma at a lower concentration than either of the compounds D or E, and so is more potent allowing for a lower plasma concentration required for a given therapeutic benefit. In addition, it is noted that the methylphenyl analogs (compounds B and D) of the chlorophenyl substituents (compounds F and C) have increased MPO IC50. Thus, it is surprising that the methylphenyl analog (compound A) has a decreased MPO IC50 versus the chlorophenyl analog (compound E).

In addition, a significant and undesirable off-target activity for any systemically-acting therapeutic agent is inhibition of the hERG potassium channel. An adverse effect of inhibition of this ion channel is well known to those skilled in the art for being associated with prolongation of the QTc interval on the patient's electrocardiogram (ECG) and potentially for the triggering of "torsades de pointes" and ventricular tachycardia (Bernard Fermini, Anthony A. Fossa, Pre-Clinical Assessment of Drug-Induced QT Interval Prolongation. Current Issues and Impact on Drug Discovery, Annual Reports in Medicinal Chemistry, Academic Press, 2004, Volume 39, Pages 323-334). A greater ratio between the concentrations required to inhibit hERG and myeloperoxidase activity (in this case hERG IC50/MPO IC50) provides an advantage as it allows for safely inhibiting MPO to a greater extent before hERG-related adverse cardiovascular effects would be encountered. This ratio is proportional to the therapeutic index (plasma concentration where an adverse effect is observed divided by the plasma concentration where the therapeutic benefit is realized). The therapeutic index, as related to hERG inhibitory activity, is an especially significant advantage for a myeloperoxidase inhibitor since an important target population is expected to be patients that have recently suffered a heart attack and thus would be much more susceptible to cardiac arrhythmia and the adverse consequences therefrom. For this reason it is especially advantageous to administer a drug with high cardiovascular safety profile to patients that are suffering from cardiovascular or coronary heart disease.

It is a significant advantage for a myeloperoxidase inhibitor candidate to have a larger ratio between the hERG IC50 and MPO IC50, in order to maximize the potential therapeutic benefit and safety ratio. In Table 1, compound A (Example 1 in this patent application) has a hERG IC50/MPO IC50 ratio of 5515 (hERG IC50=3033 uM; extrapolated from 9% at 300 uM: [300 uM×((100−9)/9)]) in comparison to that for compound D (hERG IC50/MPO IC50 ratio=162; hERG IC50=160 uM: fit to a curve including 40% at 100 uM and 63% at 300 uM) and compound E (hERG IC50/MPO IC50 ratio=260; hERG IC50=335 uM, extrapolated from 23% at 100 uM: [100 uM×((100−23)/23)]). (Extrapolation method see "Optimizing Higher Throughput Methods to Assess Drug-Drug Interactions for CYP1A2, CYP2C9, CYP2C19, CYP2D6, rCYP2D6, and CYP3A4 In Vitro Using a Single Point IC50" *J Biomol Screen* (2002) 7:373). By a similar analysis, compound F has a hERG IC50/MPO IC50 ratio of 900 (hERG IC50=1700 uM; extrapolated from 15% at 300 uM: [300 uM×((100−15)/15)]); compound C has a hERG IC50/MPO IC50 ratio of 41 (hERG IC50=33 uM; fit to a curve including 49% at 30 uM and 75% at 100 uM); and compound G has a hERG IC50/MPO IC50 ratio of 1500 (hERG IC50=900 uM; extrapolated from 25% at 300 uM: [300 uM×((100−25)/25)]). [Results for Compound B were not determined.]

Thus, compound A (Example 1 in this patent application), has an expected 34 times (i.e., 5515/162) the hERG IC50/MPO IC50 safety ratio over compound D and 21 times (i.e., 5515/260) the hERG IC50/MPO IC50 safety ratio over compound E. This exceptionally high selectivity for MPO inhibition over hERG activity with compound A offers an unexpected significant predicted cardiovascular safety advantage especially for a compound that is to be administered to patients that have a cardiovascular condition.

In an analogous manner, compound A (Example 1 in this patent application), has an expected 135 times (i.e., 5515/41) the hERG IC50/MPO IC50 safety ratio over compound C, 6.1 times (i.e., 5515/900) the hERG IC50/MPO IC50 safety ratio over compound F, and 3.7 times (i.e., 5515/1500) the hERG IC50/MPO IC50 safety ratio over compound G.

TABLE 1

MPO Activity/hERG Therapeutic Ratio

| Compound | Example No. | Structure | MPO IC50 in human whole blood | hERG IC50 (determined by curve fitting or extrapolated from % activity shown) | Therapeutic ratio hERG IC50/ MPO IC50 |
|---|---|---|---|---|---|
| A Example 1 | See Example 1 in this patent application | 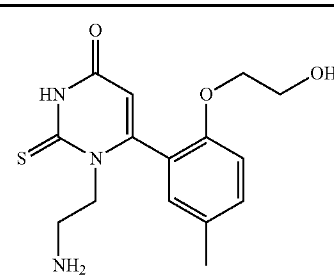 | 0.55 uM | 3033 uM (9%@ 300 uM) | 5515 |

TABLE 1-continued

MPO Activity/hERG Therapeutic Ratio

| Compound | Example No. | Structure | MPO IC50 in human whole blood | hERG IC50 (determined by curve fitting or extrapolated from % activity shown) | Therapeutic ratio hERG IC50/ MPO IC50 |
|---|---|---|---|---|---|
| B | WO130688 75 Example 164 | 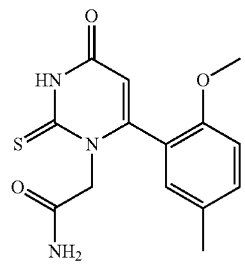 [SMILES: COc1ccc(C)cc1-c1cc(=O)[nH]c(=S)n1CC(N)=O] | 2.5 uM | Not Available | Not Available |
| C | WO130688 75 Example 63 | 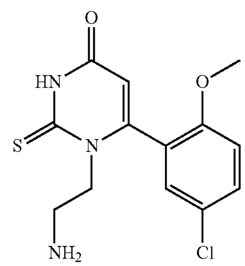 [SMILES: COc1ccc(Cl)cc1-c1cc(=O)[nH]c(=S)n1CCN] | 0.80 uM | 33 uM (49%@30 uM) (75%@100 uM) | 41 |
| D | WO130688 75 Example 159 | 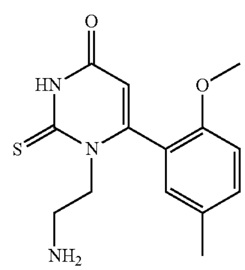 [SMILES: COc1ccc(C)cc1-c1cc(=O)[nH]c(=S)n1CCN] | 0.99 uM | 160 uM (40%@100 uM) (63%@300 uM) | 162 |
| E | WO130688 75 Example 427 | 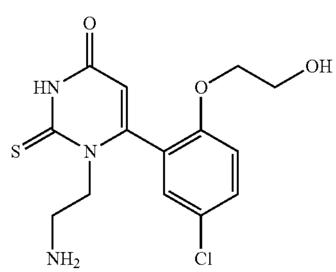 [SMILES: NCCn1c(-c2cc(Cl)ccc2OCCO)cc(=O)[nH]c1=S] | 1.3 uM | 335 uM (23%@100 uM) | 260 |
| F | Example 1 in WO130688 75 2-(6-(5-chloro-2-methoxyphenyl)-4-oxo-2-thioxo-3,4-dihydropyrmidin-1(2H)-yl)acetamide | 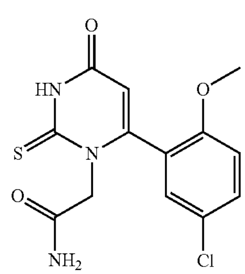 [SMILES: COc1ccc(Cl)cc1-c1cc(=O)[nH]c(=S)n1CC(N)=O] | 1.9 uM | 1700 uM (15%@ 300 uM) | 900 |

TABLE 1-continued

MPO Activity/hERG Therapeutic Ratio

| Compound | Example No. | Structure | MPO IC50 in human whole blood | hERG IC50 (determined by curve fitting or extrapolated from % activity shown) | Therapeutic ratio hERG IC50/ MPO IC50 |
|---|---|---|---|---|---|
| G | WO130688 Example 241 N-(2-aminoethyl)-2-[6-(2,4-dimethoxyphenyl)-4-oxo-2-thioxo-3,4-dihydropyrimidin-1(2H)-yl]acetamide | (structure) | 0.60 uM | 900 uM (25%@ 300 uM) | 1500 |

MPO Amplex Red Activity Assay.

MPO peroxidase activity was measured by monitoring the formation of resorufin generated from the oxidation of Amplex Red (10-acetyl-3,7-dihydroxyphenoxazine; Invitrogen, Carlsbad, Calif.) by MPO (Gomes, Fernandes et al. 2005). Assay mixtures (100 μL total volume) contained 50 mM NaPi pH 7.4, 150 mM NaCl, 1 mM DTPA (diethylenetriaminepentaacetic acid), 2% DMSO, 2 μM $H_2O_2$, 30 μM Amplex Red and the reaction was initiated by the addition of 100 pM MPO (purified from human polynuclear leukocytes and purchased from Calbiochem/EMD Biosciences, Gibbstown, N.J.). All assays were performed in 96-well, half-area, black, nonbinding surface, polystyrene plates (Corning) and the production of resorufin (excitation 530 nm, emission 580 nm) was monitored every 20 sec on a Spectramax M2 Microplate Spectrophotometer (Molecular Devices, Palo Alto, Calif.) equipped with Softmax Pro software (Molecular Devices, Palo Alto, Calif.). Reactions to determine the background reaction rate consisted of all assay components and 4 μL of 500 unit/mL bovine catalase (Sigma) in 50 mM KPi pH 7.0. The background rate was subtracted from each reaction progress curve. All data was analyzed using non-linear regression analysis in Microsoft Excel and Kaleidagraph (Synergy Software).

To determine inhibitor potency ($k_{inact}/K_I$) against MPO, the first 600 sec of the reaction progress curves were fit to equation 1, where $V_o$ is the initial rate in RFU/sec and t is time in seconds, to obtain the first order rate constant for enzyme inactivation ($k_{obs}$) at each inhibitor concentration.

$$\text{Product} = \frac{V_0}{k_{obs}} [1 - \exp(-k_{obs}t)] \quad (1)$$

Equation 1 is a variation of the standard equation for slow binding inhibition where the steady state velocity ($V_s$) is set to zero. Each $k_{obs}$ value was corrected for auto-inactivation of the enzyme by subtracting the $k_{obs}$ value for the uninhibited reaction. The corrected $k_{obs}$ values were then plotted versus inhibitor concentration ([I]) and fit to equation 2

$$k_{obs} = \frac{k_{inact}[I]}{K_I + [I]} \quad (2)$$

where $k_{inact}$ is the maximal rate of inactivation and $K_I$ is the inhibitor concentration that yields half the rate of maximal inactivation (Copeland 2005).

Thyroid Peroxidase (TPO) Amplex Red Activity Assay

TPO activity was measured using the same assay as MPO with 2 μM $H_2O_2$, 30 μM Amplex Red and the reactions were initiated with 1.3 μg of protein from HEK293 cell membranes expressing human TPO. The cDNA encoding 933 amino acids of the full length human TPO was cloned into the inducible expression vector pcDNA5/frt/to (InVitrogen), stable 293 clones were selected using 100 ug/ml of hygromycin and 15 ug/ml blasticidine in DMEM w/ 10% FBS. When cells reached 50-60% confluence, TPO expression was induced in medium containing all of above plus 10 ug/ml doxycycline and 5 ug/ml hemin (Sigma). Membranes were isolated from HEK293hTPO by harvesting the cells in PBS. The cells were pelleted at 1000×g for 5 minutes at 4° C., resuspended in homogenization buffer (1 mM sodium bicarbonate, pH 7.4) containing EDTA-Free protease inhibitor (Roche), and incubated on ice for 10 minutes followed by Dounce homogenization. Nuclei and unlysed cells were removed by pelleting at 1000×g for 10 minutes at 4° C. The supernatant was then centrifuged at 25,000×g for 20 minutes at 4° C. The pellet was resuspended in homogenization buffer and centrifuged again at 25,000×g for 20 minutes at 4° C. The final pellet was resuspended in storage buffer (50 mM Tris pH 7, 150 mM NaCl) containing protease inhibitors as described above. Membrane concentration was determined using the BCA Protein Assay (Pierce). TPO activity was measured using the Amplex Red assay as described above. Aliquots were made based on the activity accordingly and stored at −80° C.

The $IC_{50}$ values were determined by plotting the initial rates (from the first 200 sec of each reaction progress curve) as percentage of inhibition relative to the uninhibited (DMSO) reaction as a function of inhibitor concentration. The data were fit to equation 3

$$y = \frac{100}{1 + (x/IC_{50})^2} \quad (3)$$

where $IC_{50}$ is the inhibitor concentration at 50% inhibition and z is the Hill slope (the slope of the curve at its inflection point).

REFERENCES

Copeland, R. A. (2005). *Evaluation of Enzyme Inhibitors in Drug Discovery A Guide for Medicinal Chemists and Pharmacologists*. Hoboken, Wiley.

Gomes, A., E. Fernandes, et al. (2005). "Fluorescence probes used for detection of reactive oxygen species." *J Biochem Biophys Methods* 65(2-3): 45-80.

Administration of the Formula I compound (or combinations thereof) can be via any method which delivers the compound (or combinations thereof) systemically and/or locally. These methods include oral routes, parenteral, intraduodenal routes, buccal, intranasal, topical etc. Generally, the Formula I compound (or combinations thereof) are administered orally, but parenteral administration (e.g., intravenous, intramuscular, subcutaneous or intramedullary) may be utilized, for example, where oral administration is inappropriate for the target or where the patient is unable to ingest the drug.

For administration to human patients, an oral daily dose of the Formula I compound may be in the range 1 mg to 5000 mg depending, of course, on the mode of and frequency of administration, the disease state, and the age and condition of the patient, etc. An oral daily dose is in the range of 3 mg to 2000 mg may be used. A further oral daily dose is in the range of 5 mg to 1000 mg. For convenience, the Formula I compound can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 500, or 1000 mg of the Formula I compound. The total daily dose may be administered in single or divided doses and may, at the physician's discretion, fall outside of the typical ranges given herein.

For administration to human patients, an infusion daily dose of the Formula I compound may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

The Formula I compound may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjunction with the Formula I compound is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The present invention further comprises use of a Formula I compound for use as a medicament (such as a unit dosage tablet or unit dosage capsule). In another embodiment, the present invention comprises the use of a Formula I compound for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The Formula I compound (or combinations thereof) may be administered as a formulation comprising a pharmaceutically effective amount of a Formula I compound (or combinations thereof), in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use may be found in *Remington's Pharmaceutical Sciences*, 20th Edition (Lippincott Williams & Wilkins, 2000). The choice of excipient will to a large extent depend on factors such as the particular mode of administration, the effect of the excipient on solubility and stability, and the nature of the dosage form.

The Formula I compound (or combinations thereof) may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see *Remington's Pharmaceutical Sciences*, 20th Edition (Lippincott Williams & Wilkins, 2000).

Pharmaceutical compositions according to the invention may contain 0.1%-95% of the compound(s) of this invention, preferably 1%-70%. In any event, the composition to be administered will contain a quantity of a compound(s) according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: the Formula I compound and a second compound as described above. The kit comprises a means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Also, as the present invention has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

An exemplary intravenous formulation is prepared as follows:

Formulation: Intravenous Solution

| Ingredient | Quantity |
|---|---|
| Active ingredient dissolved in 5% Dextrose Injection, USP | 150 mg |
| 5% Dextrose Injection, USP | 1.0 mL |

The solution of the above ingredients is intravenously administered to a patient at a rate of about 1 mL per minute.

The active ingredient may be formulated as a solid dispersion or as a self-emulsified drug delivery system (SEDDS) with pharmaceutically acceptable excipients.

The active ingredient may be formulated as an immediate release or modified release tablet or capsule. Alternatively, the active ingredient may be delivered as the active ingredient alone within a capsule shell, without additional excipients.

General Experimental Procedures

All chemicals, reagents and solvents were purchased from commercial sources when available and used without further purification. Proton nuclear magnetic spectroscopy ($^1$H NMR) was recorded with 400 and 500 MHz Varian spectrometers. Chemical shifts are expressed in parts per million downfield from tetramethylsilane. The peak shapes are denoted as follows: s, singlet; d, doublet; t, triplet; q, quartet; m, multiplet; br s, broad singlet. Mass spectrometry (MS) was performed via atmospheric pressure chemical ionization (APCI) or electron scatter (ES) ionization sources. Observed mass (Obs Mass) reported in the Tables correspond to the exact mass of the parent molecule plus one, unless otherwise noted. Silica gel chromatography was performed primarily using a medium pressure Biotage or ISCO systems using columns pre-packaged by various commercial vendors including Biotage and ISCO. Microanalyses were performed by Quantitative Technologies Inc. and were within 0.4% of the calculated values. The terms "concentrated" and "evaporated" refer to the removal of solvent at reduced pressure on a rotary evaporator with a bath temperature less than 60° C. The abbreviation "min" and "h" stand for "minutes" and "hours" respectively.

Powder X-Ray Diffraction

Powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength K$\alpha_1$=1.54056 Å from 3.0 to 40.0 degrees 2-Theta using a step size of 0.020 degrees and a step time of 0.3 second. Samples were prepared by placing them in a silicon low background sample holder and rotated during collection. Data were collected using Bruker DIFFRAC Plus software and analysis was performed by EVA diffract plus software.

PXRD data file was not processed prior to peak searching. Using the peak search algorithm in the EVA software, peaks were selected with a threshold value of 1 and a width value of 0.3 was used to make preliminary peak assignments. The output of automated assignments was visually checked to ensure validity and adjustments manually made if necessary.

Peaks with relative intensity of 3% were summarized in Table 2. The peaks which were not resolved or were consistent with noise were not selected. A typical error associated with the peak position from PXRD stated in USP and JP is up to +/−0.2° 2-theta.

EXAMPLE 1

1-(2-Aminoethyl)-6-(2-(2-hydroxyethoxy)-5-methylphenyl)-2-thioxo-2,3-dihydropyrimidin-4(1H)-one hydrochloride

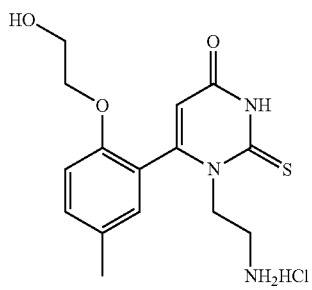

Preparation 1

1-(2-(2-Hydroxyethoxy)-5-methylphenyl)ethanone

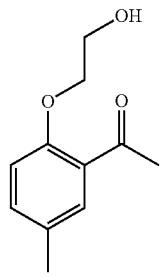

A jacketed reactor was charged with 1-(2-hydroxy-5-methylphenyl)ethanone (30.0 g, 0.200 mol, 1.0 eq) and dimethyl sulfoxide (DMSO, 210 mL), and the resulting mixture was stirred at 20° C. Cesium carbonate (200 g, 0.608 mol, 3 eq) was added followed by 2-chloroethanol (27.0 mL, 0.40 mol, 2 eq) and the resulting mixture was stirred at 80° C. until completion of the reaction. The resulting mixture was then cooled to 15° C. before water (500 mL) was added. The resulting mixture was extracted with ethyl acetate (500 mL and then 300 mL). The combined organic layers were washed with brine (300 mL) and then treated with Darco G-60 (10 g) for 1 hour at ambient temperature, before being filtered through Celite and concentrated to afford the desired product, 1-[2-(2-hydroxyethoxy)-5-methyl-phenyl]ethanone (34.35 g, 89%) as an orange oil. $^1$H NMR (400 MHz, CDCl$_3$) δ 7.53-7.48 (m, 1H), 7.29-7.22 (m, 1H), 6.91-6.85 (m, 1H), 4.21-4.15 (m, 2H), 4.02-3.94 (m, 2H), 2.83 (b, 1H), 2.62 (s, 3H), 2.31 (s, 3H). $^{13}$C-NMR (101 MHz, CDCl$_3$): δ=200.11, 159.91, 134.18, 130.64, 130.44, 128.26, 113.67, 70.69, 61.23, 31.27, 20.30.

Preparation 2

Methyl 3-(2-(2-hydroxyethoxy)-5-methylphenyl)-3-oxopropanoate

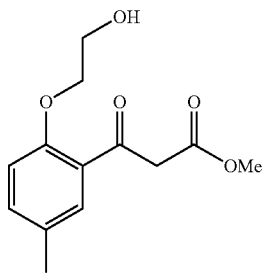 [SMILES: COC(=O)CC(=O)c1cc(C)ccc1OCCO]

A jacketed reactor was charged with potassium tert-butoxide (48.9 g, 0.427 mol) and tetrahydrofuran (170 mL) and the resulting mixture was stirred at 20° C. as dimethyl carbonate (47.1 g, 0.523 mol, 3.0 eq) was added resulting in a mild exotherm with the formation of a white slurry. To this mixture was added a solution of 1-[2-(2-hydroxyethoxy)-5-methyl-phenyl]ethanone (33.84 g, 0.174 mol) in tetrahydrofuran (170 mL) and the resulting mixture was warmed to 30° C. After 3 h, the reaction mixture was treated with a solution of acetic acid (57.5 mL, 1.00 mol) in water (338 mL). After stirring for 1 h, the reaction mixture was extracted with ethyl acetate (340 mL) and the organic phase treated with Darco (2.0 g) for 1 h at room temperature before the mixture was filtered through Celite, concentrated, dissolved in isopropyl alcohol (160 mL), and then concentrated to afford a red oil. This crude product was then taken up in isopropyl alcohol (65 mL), cooled to 0° C. and then water (120 mL) was added slowly over 15 min. After stirring for 1 h at 0-5° C., additional water (240 mL) was added over 30 min, and the mixture stirred for 30 min before the resulting solid was collected by filtration, washed with water (200 mL) and dried to afford methyl 3-(2-(2-hydroxyethoxy)-5-methylphenyl)-3-oxopropanoate (37.2 g, 85%). $^1$H NMR (400 MHz, CDCl$_3$) δ 7.69-7.65 (m, 1H), 7.33-7.27 (m, 1H), 6.89-6.83 (m, 1H), 4.16-4.11 (m, 2H), 3.99 (s, 2H), 3.98-3.93 (m, 2H), 3.71 (s, 3H), 3.53-3.40 (b, 1H), 2.30 (s, 3H). $^{13}$C-NMR (101 MHz, CDCl$_3$) δ 192.39, 169.63, 156.40, 135.46, 131.31, 130.46, 125.75, 112.39, 70.73, 60.85, 52.55, 50.26, 20.15 ppm. m/z (EI+) for C$_{13}$H$_{16}$O$_5$ 253.1 (M+H)$^+$.

Preparation 3

(Z)-Methyl 3-(2-(tert-butoxycarbonylamino)ethylamino)-3-(2-(2-hydroxyethoxy)-5-methylphenyl)acrylate

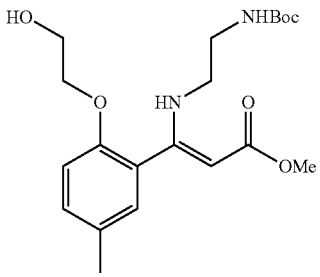 [SMILES: COC(=O)/C=C(\NCCNC(=O)OC(C)(C)C)c1cc(C)ccc1OCCO]

To a jacketed reactor was added isopropyl alcohol (250 mL), methyl 3-(2-(2-hydroxyethoxy)-5-methylphenyl)-3-oxopropanoate (36.0 g, 0.143 mol), tert-butyl 2-aminoethylcarbamate (35.0 g, 0.218 mol) and acetic acid (12.3 mL, 0.215 mol), and the mixture was heated at 84° C. After 8 h, the reaction was cooled to 15° C. and water (830 mL) was added slowly until the solution became hazy, then the addition was paused to allow solids to form over 15 min before slowly completing the water addition. The resulting slurry was stirred at 15° C. for 3 h, then filtered and the filter cake washed with water (290 mL). The solid was dried in a vacuum oven at 50° C. for 16 h to afford (Z)-methyl 3-(2-(tert-butoxycarbonylamino)ethylamino)-3-(2-(2-hydroxyethoxy)-5-methylphenyl)acrylate (51.96 g, 92%). $^1$H NMR (400 MHz, d$_6$-DMSO) δ 8.69-8.52 (m, 1H), 7.18 (dd, J=8.6, 1.6 Hz, 1H), 7.01-6.91 (m, 2H), 6.83 and 6.45 (b, total integration=1H), 4.79 (t, J=5.3 Hz, 1H), 4.25 (s, 1H), 3.99 (b, 2H), 3.67 (q, J=5.3 Hz, 2H), 3.53 (s, 3H), 3.17-2.80 (m, 4H), 2.24 (s, 3H), 1.36 (s, 9H). $^{13}$C-NMR (101 MHz, d$_6$-DMSO) δ 169.48, 162.05, 155.61, 152.99, 130.92, 129.80, 129.34, 124.32, 112.21, 82.80, 77.66, 69.84, 59.46, 49.58, 43.20, 40.53, 28.17, 19.91. m/z (EI+) for C$_{20}$H$_{30}$N$_2$O$_6$ 395.3 (M+H)$^+$.

Preparation 4 tert-Butyl 2-(6-(2-(2-hydroxyethoxy)-5-methylphenyl)-4-oxo-2-thioxo-3, 4-dihydropyrimidin-1(2H)-yl)ethylcarbamate

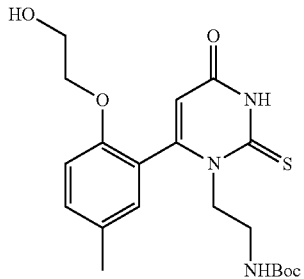 [SMILES: Cc1ccc(OCCO)c(-c2cc(=O)[nH]c(=S)n2CCNC(=O)OC(C)(C)C)c1]

A jacketed reactor was charged with butyl acetate (70 mL), (Z)-methyl 3-(2-(tert-butoxycarbonylamino)ethylamino)-3-(2-(2-hydroxyethoxy)-5-m ethylphenyl)acrylate (10.00 g, 25.35 mol) and isothiocyanatotrimethylsilane (10.0 mL, 70.98 mol). The resulting solution was heated to 80° C. and stirred for 8 hours before the reaction mixture was cooled to ambient temperature. After 12 hours, heptane (100 mL) was gradually added to the reaction mixture over a period of 10 minutes. The resulting slurry was warmed to 40° C. and stirred for 3 hours before cooling to 20° C. After 3 hours, the solids were isolated by filtration, washing with a 1:1 solution of heptane/butyl acetate (50 mL), and allowed to dry overnight. The resulting solids (9.57 g) were mixed with butyl acetate (60 mL) and the mixture stirred at 40° C. for 3 hours, then cooled to 25° C. over 30 minutes and stirred 3 hours. The resulting solids were collected by filtration, washed with butyl acetate (20 mL) and dried in a vacuum oven at 35° C. for 24 hours to afford tert-butyl 2-(6-(2-(2-hydroxyethoxy)-5-methylphenyl)-4-oxo-2-thioxo-3,4-dihydropyrimidin-1(2H)-yl)ethylcarbamate (7.75 g, 72.5%). $^1$H NMR (400 MHz, d6-DMSO) δ 12.52 (s, 1H), 7.21 (d, J=8.2 Hz, 1H), 7.07 (s, 1H), 6.97 (d, J=8.6 Hz, 1H), 6.51 (t, J=5.9 Hz, 1H), 5.62 (d, J=2.0 Hz, 1H), 4.51 (m, 1H), 3.96 (m, 2H), 3.56 (t, J=5.1 Hz, 2H), 3.47 (m, 1H), 3.35 (m, 1H), 2.86 (m, 1H), 2.23 (s, 3H), 1.27 (s, 9H). $^{13}$C-NMR (101 MHz, d6-DMSO) δ 177.53, 159.93, 155.77, 154.89, 152.96, 132.54, 131.00, 130.08, 122.89, 112.76, 109.22, 78.10, 70.44, 59.92, 50.94, 37.75, 28.69, 20.59. m/z (EI+) for $C_{20}H_{27}N_3O_5S$ 422.3 (M+H)$^+$.

Preparation 5

1-(2-Aminoethyl)-6-(2-(2-hydroxyethoxy)-5-methyl-phenyl)-2-thioxo-2,3-dihydropyrimidin-4(1H)-one hydrochloride

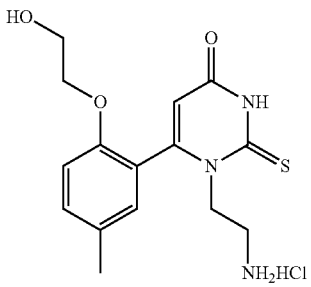

A dry 1 round bottomed flask was charged with ethanol (515 mL) and cooled to 0° C. before acetyl chloride (160 mL, 2.25 mol) was added via an addition funnel with stirring over 20 minutes. The resulting solution was then heated at 50° C. for 30 minutes and then cooled to ambient temperature. A separate 4 round bottomed flask equipped with a mechanical stirrer was charged with tert-butyl 2-(6-(2-(2-hydroxyethoxy)-5-methylphenyl)-4-oxo-2-thioxo-3,4-dihydropyrimidin-1(2H)-yl)ethylcarbamate (95.0 g, 0.23 mol) and ethanol (515 mL) to afford a white suspension. The previously prepared HCl solution in the 1 round bottomed flask was added gradually with stirring to the suspension in the 4 L round bottomed flask. The resulting mixture was stirred at ambient temperature for 20 minutes before warming to 50° C. After stirring for 1 h the reaction mixture was then allowed to gradually cool to ambient temperature and after stirring for 3 h ethyl acetate (550 mL) was added to the reaction mixture. The resulting slurry was stirred at ambient temperature for 1 h before the solids were collected by filtration, washing with a 1:1 mixture of ethyl acetate/heptane (2.5 L). The isolated solid was dried in a vacuum oven at 50° C. for 20 h to afford (1-(2-aminoethyl)-6-(2-(2-hydroxyethoxy)-5-methylphenyl)-2-thioxo-2,3-dihydropyrimidin-4(1H)-one hydrochloride (78.78 g, 98%).

$^1$H NMR (400 MHz, DMSO-d$_6$) δ: 12.82 (br. s., 1H), 7.95 (br. s., 3H), 7.32 (dd, J=8.5, 1.5 Hz, 1H), 7.17 (d, J=1.8 Hz, 1H), 7.10 (d, J=8.8 Hz, 1H), 5.76 (s, 1H), 4.88 (t, J=5.0 Hz, 1H), 4.52 (br. s., 1H), 4.06 (t, J=5.0 Hz, 2H), 3.98-4.04 (m, 1H), 3.64 (d, J=4.7 Hz, 2H), 2.93-3.01 (m, 1H), 2.86-2.93 (m, 1H), 2.28 (s, 3H); $^{13}$C NMR (101 MHz, DMSO-d$_6$) δ 177.2, 159.3, 153.9, 152.7, 132.4, 130.1, 129.8, 121.6, 112.9, 109.3, 70.1, 59.3, 47.0, 35.9, 20.0; m/z (EI+) for $C_{15}H_{19}N_3O_3S$ 322.1 (M+H)$^+$.

The powder X-ray diffraction pattern PXRD for the resulting crystalline product is provided in the FIGURE.

Table 2 below provides a PXRD peak list* for the same resulting crystalline product.

TABLE 2

PXRD peak list* for crystalline material

| Angle 2Θ (°) | Relative Intensity (%) |
|---|---|
| 8.1 | 11 |
| 9.4 | 10 |
| 10.4 | 51 |
| 11.8 | 8 |
| 15.8 | 5 |
| 16.1 | 4 |
| 16.5 | 3 |
| 17.0 | 7 |
| 18.2 | 48 |
| 18.9 | 6 |
| 21.0 | 18 |
| 21.2 | 28 |
| 21.4 | 100 |
| 22.3 | 51 |
| 22.5 | 54 |
| 22.8 | 22 |
| 22.9 | 34 |
| 23.6 | 9 |
| 23.8 | 18 |
| 24.1 | 39 |
| 24.7 | 21 |
| 25.8 | 53 |
| 26.3 | 10 |
| 27.2 | 5 |
| 27.5 | 7 |
| 27.8 | 4 |
| 28.1 | 20 |
| 28.3 | 4 |
| 28.6 | 11 |
| 29.1 | 3 |
| 29.7 | 38 |
| 30.1 | 3 |
| 30.8 | 9 |
| 31.2 | 19 |
| 31.9 | 11 |
| 32.0 | 11 |
| 32.4 | 7 |
| 32.6 | 7 |
| 34.1 | 4 |
| 34.5 | 5 |
| 34.9 | 10 |
| 35.8 | 11 |
| 36.3 | 12 |
| 36.8 | 7 |
| 37.8 | 8 |
| 38.5 | 15 |
| 39.1 | 17 |

*Note:
Characteristic peak positions were selected based on visual observation of peak shape and intensity.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention.

What is claimed:

1. A compound of the Formula I

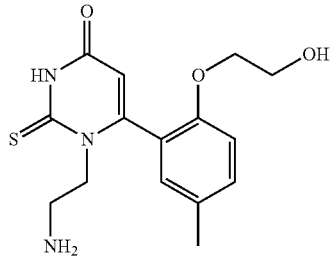

Formula I or a pharmaceutically acceptable salt thereof.

2. The hydrochloride salt of the compound of claim 1.

3. The compound 1-(2-aminoethyl)-6-(2-(2-hydroxyethoxy)-5-methylphenyl)-2-thioxo-2,3-dihydropyrimidin-4(1H)-one.

4. A method of treating cardiovascular conditions comprising administering to a mammal in need of such treatment a therapeutically effective amount of a compound of claim 1 or a pharmaceutically acceptable salt of said compound wherein the cardiovascular condition is heart failure, congestive heart failure, peripheral arterial disease, pulmonary hypertension or vasculitis.

5. A method of treating cardiovascular conditions comprising administering to a mammal in need of such treatment a therapeutically effective amount of a compound of claim 1 or a pharmaceutically acceptable salt of said compound wherein the mammal has unstable angina, coronary artery disease, stroke, atrial fibrillation, or has experienced myocardial infarction.

6. A pharmaceutical composition which comprises a therapeutically effective amount of a compound of claim 1 thereof or a pharmaceutically acceptable salt of said compound and a pharmaceutically acceptable carrier, vehicle or diluent.

* * * * *